(12) United States Patent
Torresin

(10) Patent No.: US 6,732,581 B1
(45) Date of Patent: May 11, 2004

(54) LOW THERMAL CAPACITY DEVICE FOR HIGH PRECISION POCKET-SIZE SPIROMETRY AND OTHER APPLICATIONS

(75) Inventor: Giuseppe Torresin, Padua (IT)

(73) Assignee: Biomedin, Padua (IT)

( * ) Notice: Subject to any disclaimer, the term of this patent is extended or adjusted under 35 U.S.C. 154(b) by 0 days.

(21) Appl. No.: 09/101,454

(22) PCT Filed: Jan. 13, 1997

(86) PCT No.: PCT/IB97/00012

§ 371 (c)(1),
(2), (4) Date: Jul. 17, 1998

(87) PCT Pub. No.: WO97/25920

PCT Pub. Date: Jul. 24, 1997

(30) Foreign Application Priority Data

Jan. 19, 1996 (IT) ..................................... PD96A00000A

(51) Int. Cl.[7] ................................................ G01F 1/68
(52) U.S. Cl. ................................. 73/204.14; 73/204.18; 73/861.95
(58) Field of Search .......................... 73/204.18, 204.15, 73/861.95, 204.14, 204.23, 204.25, 204.16

(56) References Cited

U.S. PATENT DOCUMENTS

| | | | | |
|---|---|---|---|---|
| 2,947,938 A | * | 8/1960 | Bennett | 324/706 |
| 3,603,147 A | * | 9/1971 | Dorman | 73/170.12 |
| 3,645,133 A | | 2/1972 | Simeth et al. | |
| 4,433,576 A | * | 2/1984 | Shih et al. | 73/204 |
| 4,445,369 A | * | 5/1984 | Stoltman et al. | 73/204.21 |
| 3,425,277 A | * | 2/1985 | Adams | 73/204.16 |
| 4,501,145 A | * | 2/1985 | Boegli et al. | 73/204 |
| 4,576,050 A | * | 3/1986 | Lambert | 73/861.05 |
| 4,691,566 A | * | 9/1987 | Aine | 73/204.26 |
| 5,058,426 A | * | 10/1991 | Kobayashi | 73/204.26 |
| 5,080,165 A | * | 1/1992 | Engelhardt | 165/46 |
| 5,090,241 A | * | 2/1992 | Kobayashi | 73/204.26 |
| 5,277,196 A | | 1/1994 | Hankinson et al. | 73/202.5 |
| 5,582,628 A | | 12/1996 | Wood | |
| 6,247,495 B1 | * | 6/2001 | Yamamoto et al. | 73/202 |

FOREIGN PATENT DOCUMENTS

| | | |
|---|---|---|
| HU | 208734 B | 4/1990 |
| WO | 94/28788 | 12/1994 |
| WO | 95?10980 | 4/1995 |

* cited by examiner

Primary Examiner—Harshad Patel
(74) Attorney, Agent, or Firm—Hoffman, Wasson & Gitler

(57) ABSTRACT

The spirometer has a low thermal capacity. A circuit supplies power to the spirometer in pulses to heat the spirometer to body temperature. The circuit senses the temperature of the spirometer between intervals. The circuit can also be used in a calorimeter to measure the heat exchange during chemical reactions using the palladium hydrogen. The heating and sensing functions are performed by a single element to result in a small pocket sized device. The portability of the device increases its usefulness.

18 Claims, 6 Drawing Sheets

LOW THERMAL CAPACITY DEVICE FOR HIGH PRECISION POCKET-SIZE SPIROMETRY AND OTHER APPLICATIONS

TECHNICAL FIELD

This invention refers to the fields of spirometry measurements and in particular to thermostatic control of pneumotacographs. Furthermore, it can also be conveniently used in both micro-calorimetry and in the measurement of flow rates of a fluid along a pipe.

BACKGROUND ART

It is common practice to monitor lung function by analysing sample breath performance. As humans live breathing, it is easy to observe that our breaths are not all exactly the same and that even lung function may change depending on a wide range of variable factors. This is especially true in the case of particular environments or of special reactions to certain volatile or suspended agents, or of respiratory pathologies in progress.

Lung volume is one of the most informative measurements that can be performed from the breath. Variations of volume allow estimating and predicting the profile of the lung functionality and are therefore crucial towards a proper and prompt treatment.

Since lung volume is on the order of several liters, it is impractical to measure it directly. The flow can be measured instead—e.g. from the pressure drop across a resistance—and then integrated to obtain volume readings. This can be done reliably only to the extent in which the flow-measuring device is linear and accurate. Measuring flow instead of volume allows reducing the size and weight of spirometric devices. However, measuring flow entails a variety of technical problems mainly related to thermostatic regulation, which we examine below.

In 1925 A. Fleisch proposed what is still one of the most accurate methods to perform spirometry by means of measuring laminar flows. To that end, Fleisch used a honeycomb structure. The most common form of honeycomb structure consists of a cylinder made by coupling and rolling up two thin metal sheets, one corrugated and the other smooth, around a tiny hub.

The metal sheets are made of brass and the dimensions of the resulting cylinder can be of diameter=42 mm, height=32 mm (Fleisch No. 4), the pressure drop is measured around the outer ring of the cylinder at a distance of 20 mm.

The honeycomb structure is one of the many possible physical filters capable of maintaining a laminar flow in a conduit, so that pressure drop and flow rate values are linearly correlated. Following the Fleisch method, several other different structures have been introduced. The most widely known is that of the fine mesh screen structure. This is lighter than the honeycomb structure but "frequent cleaning and re-calibration are considered essential to preserve accuracy in measurements"([1]).
Notes:
[1]) *Office Spirometry*, P. L. Enright, R. E. Hyatt Lea & Febiger, 1987

The temperature of the air inside human lungs is 37° C. and saturated with water vapor. When exhaled, air condenses and releases its vaporisation enthalpy.

To maintain a temperature of 37° C., Fleisch and his successors chose to heat their structures by means of an external heater. As a matter of fact, the approximately 6.5 Watts required to heat a classical size 4 Fleisch cylinder, which is also due to heat inefficiency factors and to the high thermal inertia of the whole assembly, has up until recently made it difficult to produce a truly portable heated pneumotach system.

As portable instruments cannot conceivably feature such high values of power consumption, in recent years several non-heated spirometry instruments and pneumotacographs have been proposed.

One particularly serious difficulty that has arisen with the widespread use of non-heated flow transducers is vapor condensation.

This factor slightly affects flow cooling, as condensing vapor releases its vaporisation enthalpy, though the main point is that turbulence occurs and this means that the flow is no longer linear. As turbulence implies a quadratic relationship between the pressure drop and flow rate, flow readings can be seriously flawed. This source of error makes the non-heated systems unreliable in a very subtle way.

Spirometry is a test consisting of several repeated trials and for each trial condensing vapor releases its vaporisation enthalpy. After a small number of maneuvres referring to a single patient's test, the instrument tends to accumulate water vapor, hence the air flow becomes turbulent, and measurement overestimation increases. According to the rules suggested by the American Thoracic Society and the European Respiratory Society, the highest value achieved in a series of maneuvres has to be kept as the spirometry measurement result. So any overestimation error occurring during the test leads to globally wrong results. The recent increase of unreliable spirometric results is strongly related to the widespread use of non-heated pneumotach systems.

Ceramic honeycombs had been introduced in an attempt to solve this problem, though without success, as these tended to absorb water vapor ([2]). They were also quite heavy and temperature had to be measured with extremely delicate, lightweight elements, besides creating difficulties indisinfecting.
[2]) U.S. Pat. No. 5,277,196 January 1994 Hankinson et al. 128/725

The present state-of-the-art provides a wide choice of solutions that exhibit technical drawbacks, which have heavily delayed the production of a simple, reliable, small, lightweight, low-power, easy-to-clean and truly portable pneumotach system.

Similar problems also occur with those instruments which measure heat exchanges in physical (fluid flow rate measurement) and/or chemical processes especially in gas-solid interactions (Palladium-Hydrogen interaction).

In fluid flow rate measurements, with constant direct measurement techniques, problems arise when flow rate changes rapidly and the fluid temperature is variable (e.g. like the case of blood flowing through a vessel ([3])). On the other hand, techniques that separate the heat source (emitter) from the measuring device (sensor) have evident disadvantages in that the sensor collects only a small fraction of the signal emitted.
[3]) Baxter Int. Inc., WO 94/28788 December 1994

Another case where thermostatic regulation is crucial is in the interaction Palladium-Hydrogen. In this case, the measurement concerns the enthalpy release accompanying the absorption of hydrogen into a Palladium layer and (on the basis of literature data) the determination of the amount of hydrogen absorbed by the sample ([4]). In this case, the calorimeter used to enclose the environment where the reaction takes place tends to be rather bulky, features a slow response and its cost is proportional to the precision to be achieved by the measurement. On the other hand, the use of small elements as thermistors([5]), platinum wires([6]) or macromachined structures, exhibits difficulties related to the surface where the reaction takes place. Whenever a large surface is needed as in measurements of gas adsorption enthalpies, accurate measurement becomes problematic. These determinations can in fact involve very low thermal effects and low thermal conductivity substrates whereby punctual measurements cannot be applied.

[4]) Lewis F. A., *The Palladium Hydrogen System*, Academic Press 1967
[5]) U.S. Pat. No. 3,645,133, (SIMETH) 29 Feb. 1972
[6]) WO, A, 95/10 980, (MEDTRAC) 27 April 1995

DISCLOSURE OF INVENTION

The purpose of this invention is to produce a device with at least one active element featuring low heat capacity, that may be used especially as a space-saving instrument for measuring and controlling heat exchanges.

The invention relates, as defined in claim 1, to a device based on an element of low heat capacity, suited for monitoring and controlling the temperature of a certain environment. Power is supplied in pulses to this element while heat relaxation analysis during the intervals between pulses is performed on the element itself.

When it is set up for spirometry and calibrated for normal body temperatures, the device becomes a pocket-size instrument featuring high precision and low power consumption. With appropriate adaptations the same device may also be used either for high precision flow rate or high sensitivity calorimetry.

Other unique features of this invention appear in the description that follows.

DETAILED DESCRIPTION OF THE INVENTION

Further on, a detailed description is provided with several examples of application and reference to enclosed figures. Enclosed illustrations:

FIG. 1 a honeycomb structure, built in accordance with the concept of this invention, obtained by rolling together two different foils.

FIG. 2 an electric circuit diagram, showing the microcontroller and a digital switch for heating the honeycomb structure shown in FIG. 1.

The preferred embodiment of the present invention comprises a substrate consisting a strip of stainless steel foil of 5–20 microns in thickness, shaped accordingly for the kind of application.

This substrate is excited by means of a pulse width modulation power supply unit and measurements of temperature of the heater itself are performed during its thermal relaxation phase between adjacent pulses.

Figure 1:
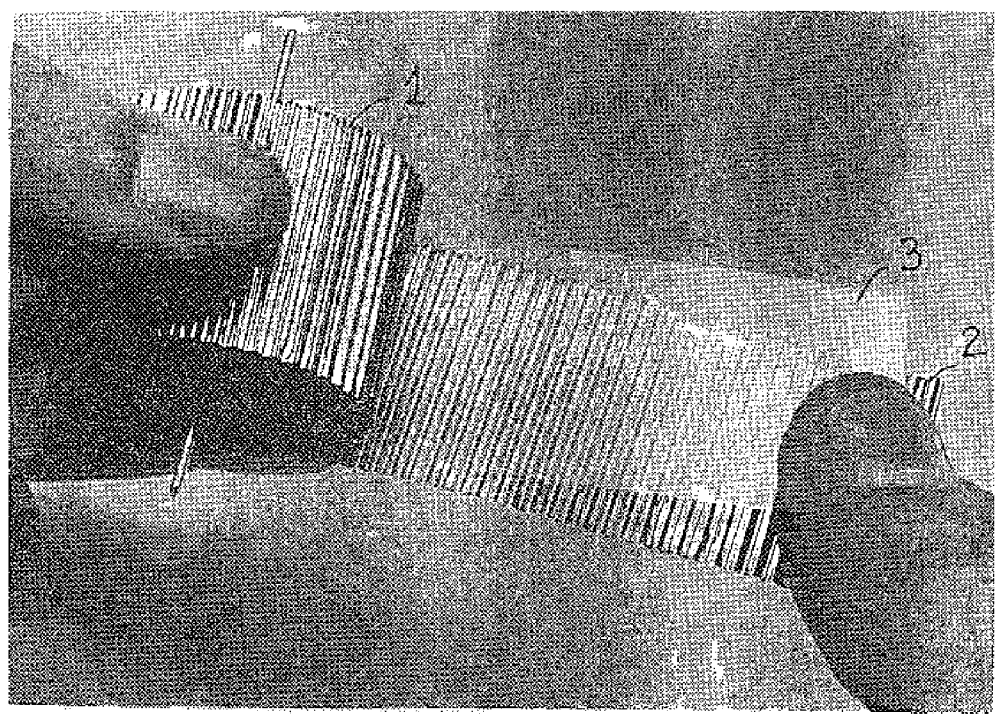

FIG. 1 shows a composite Fleisch honeycomb structure (1) made according to the concept of present invention.

This consists of a structure obtained by rolling together two overlapping foils (2), (3), one of which is corrugated to obtain a honeycomb structure. One of the two foils is conductive (2) (i.e. made of stainless steel, from 0.01 to 0.05 mm in thickness, preferably 0.02 mm) and features a resistance value (2–3 Ohms with a temperature coefficient of some hundreds of microohms per ° C.) that makes it suitable for fast heating to the operating temperature by means of hand-held, low-power batteries. The other foil is a corrosion-proof insulator (3), capable of withstanding heat overloads up to 120° C. in order to allow thermal disinfection.

Figure 2:
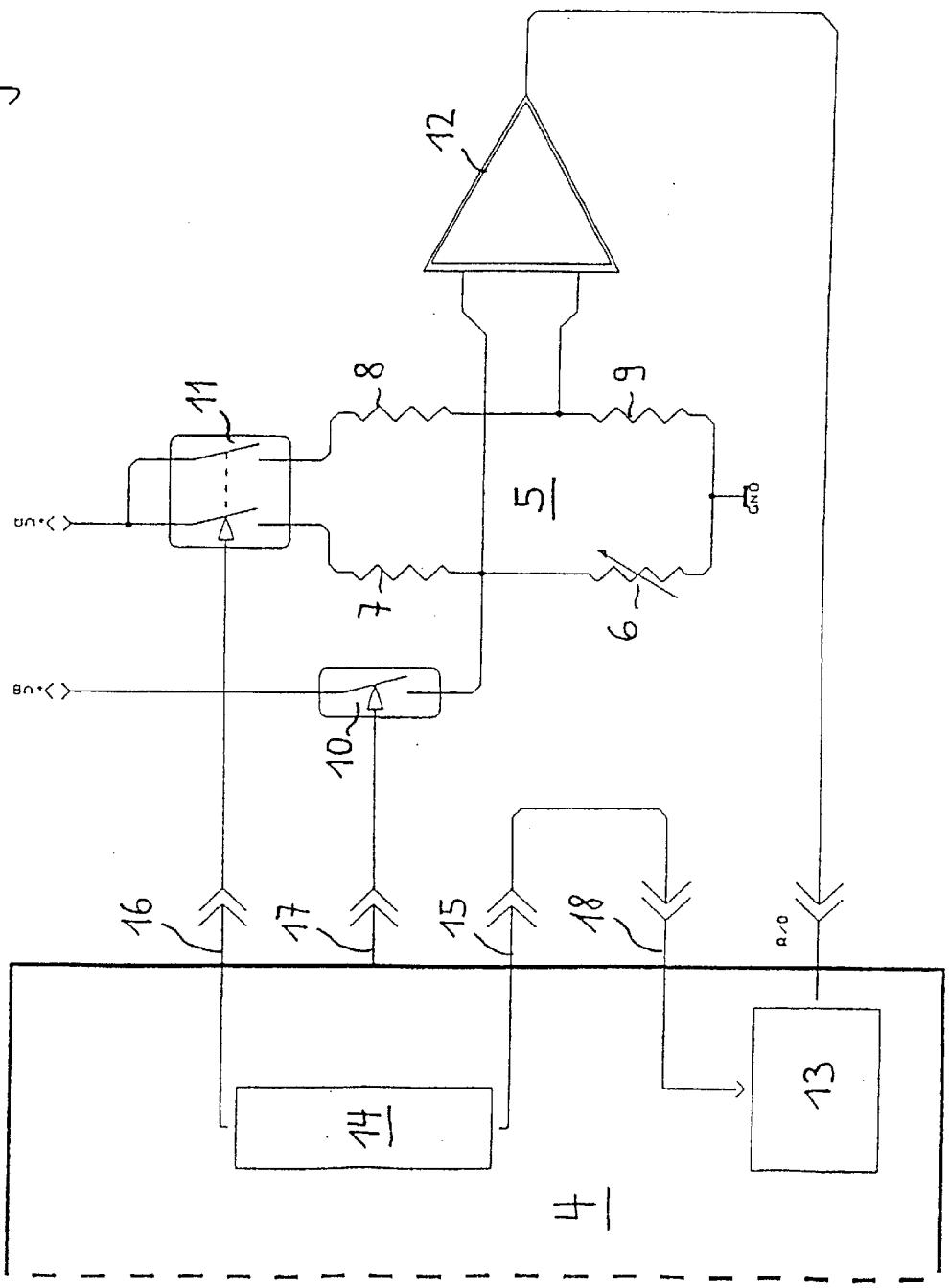

FIG. 2 shows an electrical circuit diagram representing the concept of this invention. This circuit is used to heat the Fleisch honeycomb structure shown in FIG. 1 as well as for other applications. It consists of a microcontroller (4), a bridge (5) with a heating/sensor element (6) on one branch and temperature-invariant resistors (7), (8) & (9) on the other branches, a switch (10) for connecting the power supply to the heating/sensor element (6) for the heating phase, a double switch (11) for supplying power to the bridge (5) for measuring thermal relaxation of the heating/sensor element itself (6) when the heating phase is not active, an instrumentation amplifier (12) for collecting bridge signals, which is then connected to the analog-digital converter (13) incorporated inside the microcontroller (4).

Figure 3:
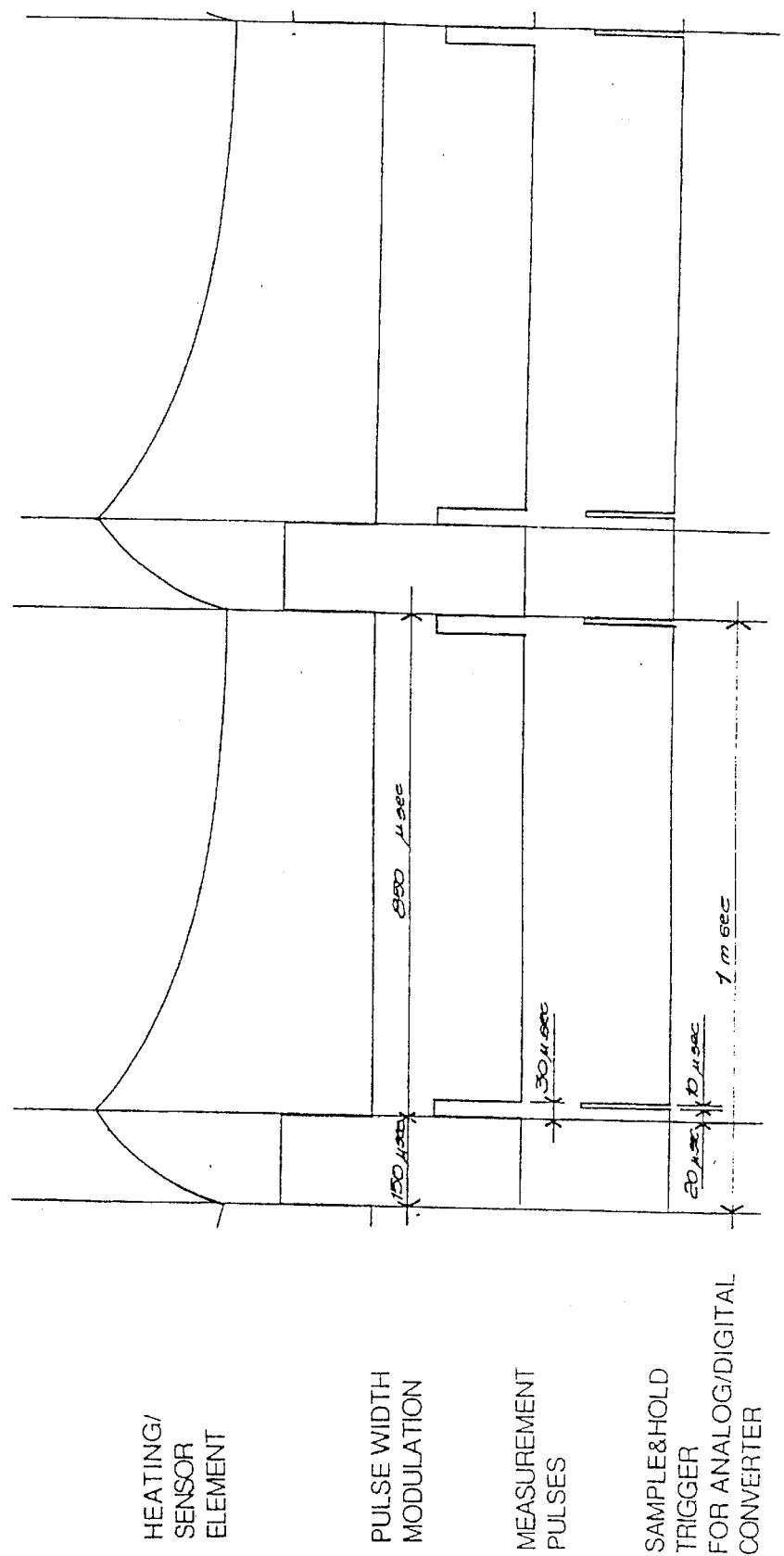
FIG. 3 represents the operating principle of the system, in accordance with the concept of this invention.

FIG. 3 provides a general description of how the system works. The digital power switch is turned on for 150 microseconds, whereas thermal relaxation of the element takes place for the remaining 850 microseconds of the duty cycle. During the 150 microseconds in which power is supplied, the element heats up. The temperature trend depends on the voltage and time. The time period of 150 microseconds can be increased or decreased depending on whether more or less heat is needed, whereas the 1-millisecond time separation between pulses is maintained constant.

At the end of the heating pulse the measuring phase begins. This consists of one or more measurements during the thermal relaxation. For example purposes, two measurements at the beginning and end of the relaxation phase (FIG. 3) have been indicated. The microcontroller (4) issues a measurement pulse that is long enough to ensure stabilisation of the operational amplifier (12) for the measuring phase (i.e. 20 microseconds). At this time, the same pulse, delayed by the amplifier stabilisation time (12), is returned to the sample&hold circuit (S/H) of the 10-bit analog-digital converter (13) incorporated inside the microcontroller itself (4). The power supply to the bridge is switched off 10 microseconds after the S/H pulse which enabled the acquisition of the bridge amplifier signal. This supply period is kept short compared to the total relaxation time in order to reduce interference in the heating/sensor element.

Figure 4:
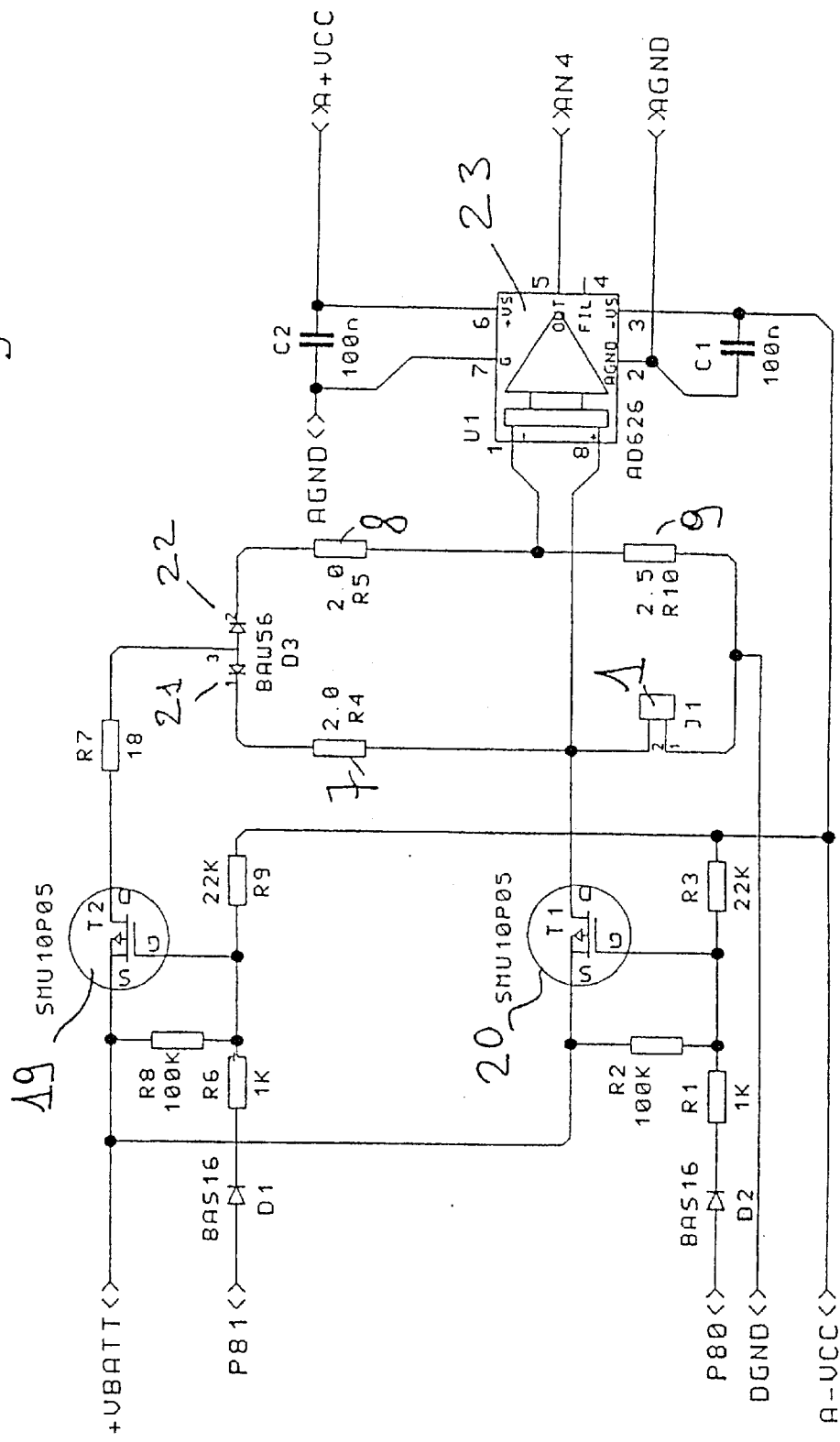
FIG. 4 shows the electric circuit diagram, with MOSFET transistors, which control the temperature of the honeycomb structure.

FIG. 4 shows the electrical circuit diagram for temperature calibration of the Fleisch honeycomb structure. In this case, the digital switches are substituted by MOSFET transistors (19), (20). The Fleisch power supply works as if it were a switch as shown in FIG. 2, whereas bridge power is supplied by means of a second MOSFET. A fast diode (21) situated at the top of the bridge facing towards the branch of the Fleisch structure completes the double switch function as it prevents the current from passing through the other branches of the bridge while the Fleisch structure (1) is in operation.

A second fast diode (22) similar to the first is placed at the top of the bridge facing towards the other branch to ensure the same voltage drop in the two branches while the bridge is in operation. The amplifier gain value (23) is programmable. This can be increased when the signal is low and the 10-bit definition of the converter is unable to ensure sufficiently accurate measurements.

Figure 5:
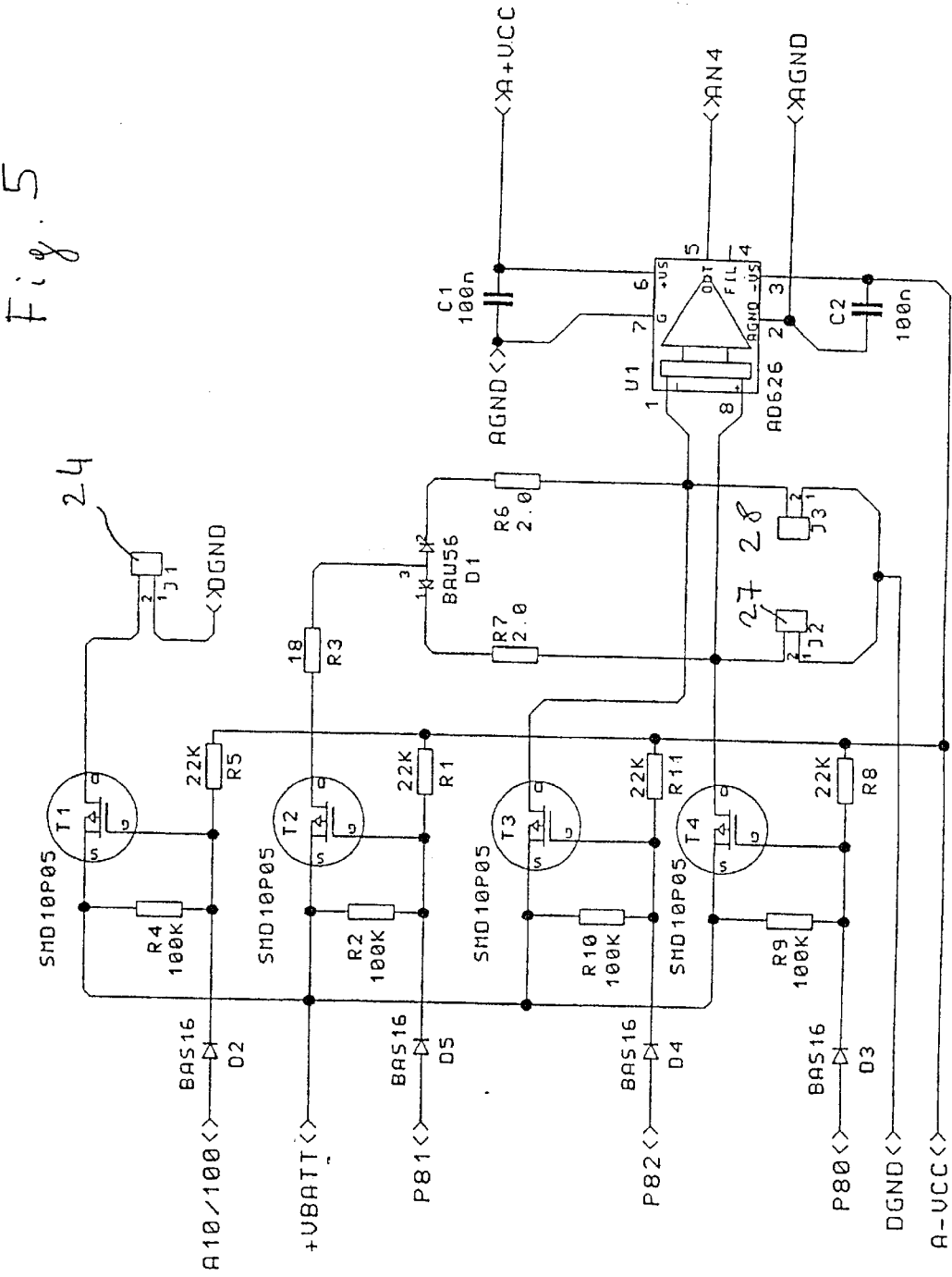
FIG. 5 shows the circuit used in the experiment for the reaction between Palladium and Hydrogen.

The circuit in FIG. 5 is used in a calorimeter for the Palladium-Hydrogen interaction experiment. It has a solenoid valve which is used to introduce 200 mbar of hydrogen into the calorimeter. The bridge has two opposite branches (27, 28) that are activated with heating times which can differ, so that the bridge can be kept in balance as better clarified further on.

Figure 6:
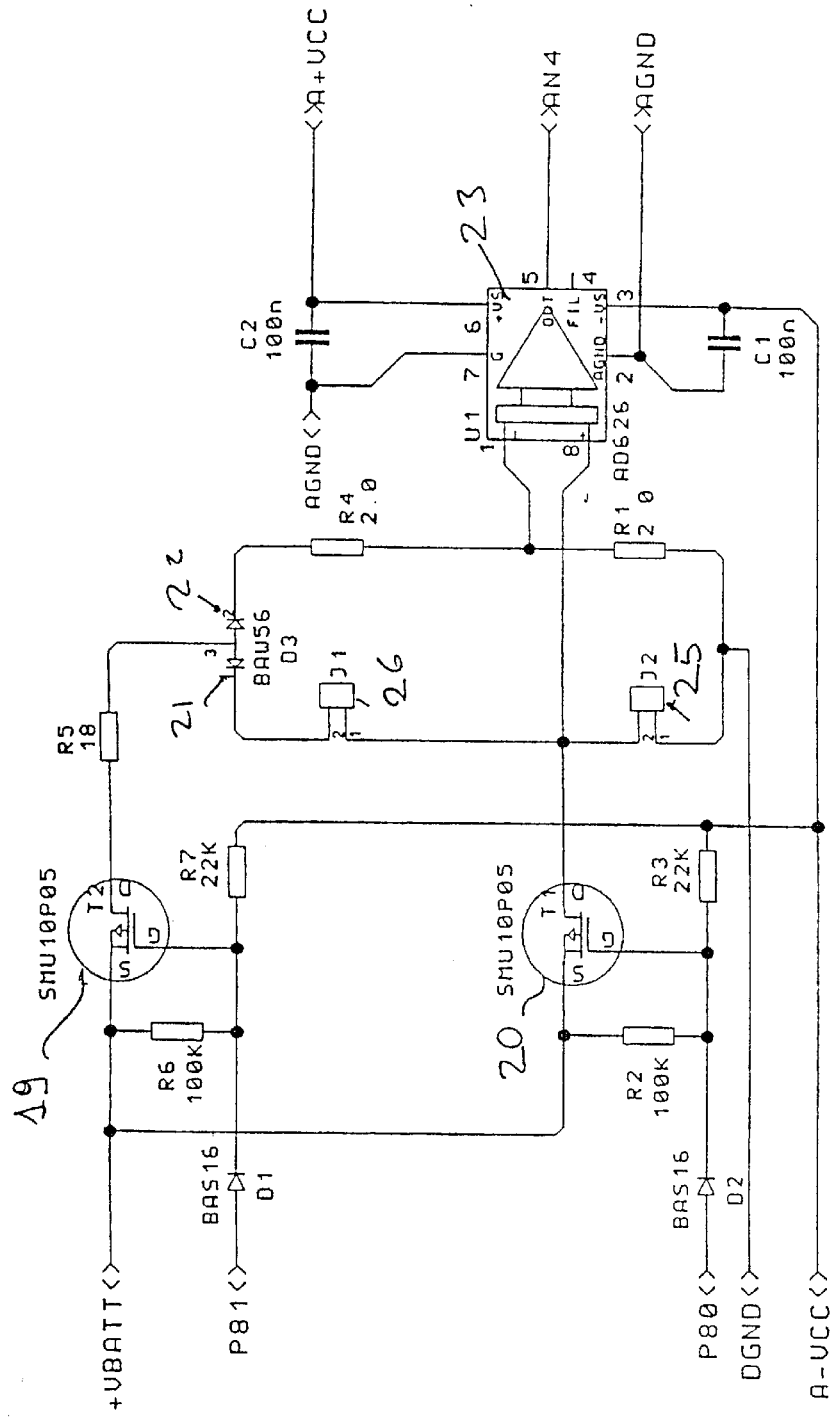
FIG. 6 shows a circuit for measuring flow rates.

The circuit shown in FIG. 6 is similar to that shown in FIG. 4 except for the reference element (26) which substitutes the temperature-invariant resistor in the bridge branch where the heating/sensor element is located, collects data regarding the fluid temperature and provides an output signal that is already filtered from the influence of temperature.

As far as the Fleisch honeycomb filter in FIG. 1 is concerned, it is evident that the thermal inertia of the conductive sheet (2) is low (it weighs less than 10 grams) and enables fast heating to body temperature. Cold-start setting of the instrument can be performed within 30 seconds for a Fleisch No. 4 size structure, and temperature calibration can be stopped immediately after the test, as well as the related power supply, which can be reduced to its new lighter duties.

The transducer is maintained free from condensed vapor, which is crucial towards rendering the measurement robust to environmental conditions (humidity) and indispensable during intensive testing (exhaled air is saturated with water vapor). In addition, it can be sterilized on the spot by heating it up to 120° C. for a few seconds, or removed for cleaning with disinfectants.

Previous descriptions referring to the honeycomb filter can also be applied to the fine mesh screen in the same way, the only difference being that in this case there are wires instead of sheets.

Another preferred embodiment that is suitable for performing high sensitivity calorimetric measurements (as indicated in FIG. 5) is described by the following experiment. The heating/sensor element has been enclosed in a reactive chamber equipped with inlet/outlet valves enabling either evacuation of the chamber or introduction of the selected gas.

The sensor element consists of a 5-micron stainless steel foil. For this, taking into account a weight of 8 g/cm$^3$ and a specific thermal capacity of 0.1 cal/g referring to a unit area of 1 cm 2, we have a thermal capacity≅400 $\mu$cal/° C. cm$^2$.

With reference to the same strip area heated at 60° C. (remembering that the exchange surface of the strip is two times the unit area), we have a thermal flow in Helium atmosphere at 25° C. of 2.4 mW/° C. cm$^2$≅576 $\mu$cal/° C. cm$^2$ sec (giving a thermal flow through exchange surface for a 35° C. gradient equal to 20,160 $\mu$cal/cm$^2$ sec). The loss of radiation per cm$^2$, taking into account an emission factor for a polished surface of 4% is 5.67×10$^{-12}$×0.04×333$^4$≅27.89×10$^{-4}$ Wo≅669.31 $\mu$cal/cm$^2$ sec.

The heater/sensor temperature (solid-gas phase) is calibrated to 60° C. by means of the PWM power supply and adopting a frequency range from 1 to 10 kHz and accepting a ripple less than 1° C. around the mean value of 60° C.

With a Palladium-coated (0.1 micron) strip we obtain 0.12 mg/cm$^2$ weight and 7 microcalories/° C. cm$^2$ thermal capacity. Once the steady state condition is reached, 200 mbar of hydrogen are introduced into the chamber and the sample temperature is monitored according to the described procedure. Since 0.12 mg of Palladium corresponds to 1.12×10$^{-6}$ mol and the hydrogen absorption enthalpy is ~9 kcal/mol, a measured enthalpy of 3000 microcalories makes it possible to estimate that the Pd coating has been converted in into Pd Hydride, represented by the stoichiometric formula Pd H$_{0.6}$. The rapidity of this process well suits the geometric features of the sample according to the approximated formula.

$$\text{Diffusion time} = \frac{(Pd\ thickness)^2 \{cm\}}{(Diff\ coeff.)\{cm^2\ sec^{-1}\}} = \frac{(1\times 10^{-5})^2}{\sim 10^{-7}} \simeq 1\ msec$$

This also describes the benefits introduced by the device, which is capable of monitoring even rapidly evolving processes.

A further improvement in accuracy of the measurement can be achieved by using the device in a differential manner as indicated in FIG. 5. Here two strips, one Pd coated (27) and one used as reference (28) are simultaneously connected to the PWM supply with independent circuits. The PWM frequency ranges from 1 to 10 kHz and thermal relaxation is measured twice at the beginning and at the end of the free thermal evolution of the element.

The differential signal thus collected provides the heat variation on one branch of the bridge with high sensitivity. This technique can be even further improved by introducing a servo-loop and appropriate processing by the microcontroller. In this case, the duty cycle of the PWM supply to the Pd coated strip is continuously adjusted in order to maintain the bridge in equilibrium and the power differences between the two PWM supplies provides an immediate indication of the amount of heat exchanged.

The proposed device is also particularly useful for application as versatile high precision flow meters. Heat loss by convection in a meter stream from a strip oriented along the direction of the fluid depends on the temperature gradient between the strip and the fluid, according to $$Q/S = h(t_{pl} - t_F)$$

where
Q=heat loss S=surface $t_{pl}, t_F$=plate and fluid temperature
h=heat loss coefficient.

Accepting on an empirical ground that for water flowing at a rate u (fluid velocity in cm/sec) below 200 cm/sec, h is given by $$h \cong 2.8\times 10^{-6} u\ cal/°\ C.\ cm^2\ sec$$

it is possible to determine that, within typical boundary conditions of $t_{pl}$=47° C., $t_F$=37° C. fluid velocity from 1 to 100 cm/sec leads to a heat exchange rate ranging from 28 to 2,800 microcalories per millisecond per square cm. Such large heat exchange values provide a great flexibility in facing several different real world problems, by handling both PWM frequency and substrate dimension. The same technique works also for measuring blood velocity in vivo in blood vessels.

The above calculation can obviously be simplified, by merely substituting one of the temperature-invariant resistors on the same side of the heated strip with an identical strip which plays a role only in the measurement process but not in the heating process, as shown in FIG. 6.

Reference numbers in Figures 1 honeycomb structure (active element)
2 corrugated conductor foil
3 insulator foil
4 microcontroller
5 bridge for measurements (high precision resistor bridge)
6 heating/sensor element
7 temperature-invariant resistor
8 temperature-invariant resistor
9 temperature-invariant resistor
10 digital switch
11 double digital switch
12 signal amplifier
13 analog/digital converter
14 time delay device
15 delayed measurement pulse output
16 measurement pulse output
17 heating pulse output
18 sample&hold input
19 mosfet transistor
20 mosfet transistor
21 diode
22 diode
23 signal amplifier
24 solenoid valve 25 active heating element (current measurement device)
26 reference element
27 active reference element.
28 active element for differential operation

What is claimed is:

1. A device, comprising:
    a substrate, said substrate functioning as a heating and temperature sensor, said substrate being thermally conductive and electrically temperature dependent resistive and having a surface to volume ratio greater than ten, and
    a circuit supplying power to said substrate in pulses, said circuit arranged to sense the temperature of said substrate during intervals between said pulses.

2. A device according to claim 1, wherein said circuit has a temperature invariant resistor, the temperature of the substrate is measured by comparing electrical resistance of said substrate to that of said temperature-invariant resistors by bridge measurement techniques.

3. A device according to claim 1, arranged to be used for spirometry measurements where the inhaled and exhaled air is maintained at body temperature, wherein the substrate comprises a composite honeycomb structure built according to "Fleisch geometry", said structure being obtained by coupling insulating and conductive layers.

4. A device according to claim 1, arranged for measuring the flow rate of a fluid, wherein the flow rate is measured by one or more appropriate heating and sensing element consisting of thin metal strip supplied with power of means of a pulse modulating circuit, and the flow rate is determined by measuring the thermal relaxation between the pulses of the circuit.

5. A device according to claim 1, adapted for calorimetric measurement of heat exchanges occurring in solid-gas reactions, wherein the substrate comprises a metal sheet featuring very low thermal capacity and coated with thin layers of a chosen solid, and the substrate is supplied with power by a pulsed supply and the enthalpy of the chosen solid-gas reaction is determined by measuring the thermal relaxation between modulated pulses.

6. The apparatus of claim 1, wherein said circuit comprises a microcontroller, a bridge having a heating and sensing element on one branch and temperature invariant resistor on the other branches, a switch for connecting the power supply to said heating and sensing element, and a double switch for supplying power to the bridge for measuring thermal relaxation.

7. The apparatus of claim 6, wherein said switch is a MOSFET transistor and said double switch is a MOSFET resistor and a fast diode.

8. The apparatus of claim 1, wherein said substrate is a calorimeter.

9. A measuring system, comprising a honeycomb structure, formed by rolling together two overlapping foils, ore of which is knurled, corrugated or folded and the other smooth, to form a plurality of passages therebetween, one of the foils being an insulator and the other being a heating and sensing element of low thermal capacity and of a resistance characteristic wherein said honeycomb structure is rapidly heated by means of a dry cell, low-capacity or rechargeable type batteries, and a circuit, connected to said honeycomb structure and arranged to supply power to said honeycomb structure in pulses, so that it is heated and caused to heat the surrounding environment during said pulses, said circuit being arranged to sample the temperature of said heating and sensing element during the thermal relaxation intervals between said pulses, wherein said heating and sensing element forms part of a bridge circuit, by which the resistance of said honeycomb structure is compared with constant temperature reference resistors forming part of said bridge.

10. A low thermal capacity apparatus for high precision spirometric applications, such apparatus comprising:
    a) a heating/sensing element,
    b) said heating/sensor element being formed of two overlapping foils,
    c) one of said foils being corrugated, and the other of said foils being smooth, so that a honeycomb shape is achieved,
    d) one of said foils possessing electrical insulating properties, while the other foil possesses electrical conductive properties,
    e) a circuit connected to said heating/sensing element,
    f) said circuit including an electrical bridge with said heating/sensor element connected in one branch of said bridge and temperature reference means connected within other branches of said circuits,
    g) a power source for supplying power to said circuit to heat the conductive foil of said heating/sensor element and the surrounding environment,
    h) pulse modulation means for controlling the on-off cycle of operation of said power source,
    i) said heating/sensor element measuring the temperature of said electrically conductive layer during thermal relaxation intervals when the power source is switched off,
    j) and said measured temperature is compared to the temperature established by said temperature reference means.

11. A low thermal capacity apparatus as defined in claim 10 wherein said temperature reference means comprises temperature-invariant resistors.

12. A low thermal capacity apparatus as defined in claim 11 wherein said power source comprises low-power batteries.

13. A low thermal capacity apparatus as defined in claim 12 wherein said insulating foil is corrosion-proof and can withstand heat overloads up to 120° C. to allow thermal disinfection.

14. A low thermal capacity apparatus as defined in claim 10 wherein said conductive foil is made of stainless steel, and is 0.01–0.05 mm in thickness.

15. A low thermal capacity apparatus as defined in claim 10 further including first switching means for connecting said power supply to said heating/sensing element during the heating phase of the cycle of operation.

16. A low thermal capacity apparatus as defined in claim 10 further including second switching means for supplying power to said bridge for measuring thermal relaxation of the heating/sensing element when the heat phase of the cycle of operation has been terminated.

17. The apparatus as defined in claim 10 wherein the electrically conductive foil is made of stainless steel, and is 0.01 to 0.05 mm in thickness.

18. The apparatus as defined in claim 10 wherein the foil possessing electrical insulating properties is corrosion proof, and is capable of withstanding heat overloads up to 120° C. to allow thermal disinfection.

* * * * *